(12) United States Patent
Ranatunga et al.

(10) Patent No.: US 10,413,567 B2
(45) Date of Patent: Sep. 17, 2019

(54) SHEAR-THINNING HYDROGEL, KIT AND METHOD OF PREPARATION

(71) Applicant: OUROTECH, INC., Dover, DE (US)

(72) Inventors: Duleeka Nimantha Bandara Ranatunga, Mississauga (CA); Andrew Christopher Wenger, Kitchener (CA); Zhi Yuan (William) Lin, Toronto (CA)

(73) Assignee: OUROTECH, INC., Dover ( * ) Notice: Subject to any disclaimer, the term of this patent is extended or adjusted under 35 U.S.C. 154(b) by 0 days.

(21) Appl. No.: 15/637,002

(22) Filed: Jun. 29, 2017

(65) Prior Publication Data

US 2017/0312306 A1 Nov. 2, 2017

Related U.S. Application Data

(63) Continuation of application No. PCT/IB2017/050460, filed on Jan. 27, 2017.

(Continued)

(51) Int. Cl.

| | |
|---|---|
| *C08J 3/075* | (2006.01) |
| *A61K 31/74* | (2006.01) |
| *A61L 27/52* | (2006.01) |
| *C08J 3/24* | (2006.01) |
| *C08K 5/1545* | (2006.01) |
| *C08L 5/04* | (2006.01) |
| *C08L 5/08* | (2006.01) |
| *A61K 9/00* | (2006.01) |

(Continued)

(52) U.S. Cl.
CPC ............ *A61K 31/74* (2013.01); *A61K 9/0024* (2013.01); *A61K 31/724* (2013.01); *A61K 38/02* (2013.01); *A61K 47/22* (2013.01); *A61K 47/26* (2013.01); *A61L 27/20* (2013.01); *A61L 27/52* (2013.01); *A61L 31/048* (2013.01); *C08J 3/075* (2013.01); *C08J 3/24* (2013.01); *C08J 3/243* (2013.01); *C08K 5/1545* (2013.01); *C08L 5/04* (2013.01); *C08L 5/08* (2013.01); *C08J 2305/04* (2013.01); *C08J 2405/08* (2013.01)

(58) Field of Classification Search
None
See application file for complete search history.

(56) References Cited

U.S. PATENT DOCUMENTS 9,364,545 B2    6/2016   Jhan et al.

FOREIGN PATENT DOCUMENTS

| WO | 2014/028209 A1 | 2/2014 | |
| WO | WO 2015 050943 | * 4/2015 | ............ A61F 13/02 |

OTHER PUBLICATIONS

Lee et al., Macromolecules, 2016, vol. 49, pp. 7450-7459.*

(Continued)

*Primary Examiner* — Brian Gulledge
(74) *Attorney, Agent, or Firm* — Perry + Currier Inc

(57) ABSTRACT

A shear-thinning hydrogel composition includes: a first polymer chain including: (i) a first plurality of units each having at least one of a monosaccharide and an amino acid; and (ii) a cross-linking group bound to the at least one of the monosaccharide and the amino acid of one of the first plurality of units via conversion of a carboxyl group of the unit to a peptide bond; a second polymer chain including a second plurality of the units; and a cross-linking additive connecting one of the second plurality of units to the first polymer chain via the cross-linking group.

9 Claims, 16 Drawing Sheets

Related U.S. Application Data

(60) Provisional application No. 62/288,778, filed on Jan. 29, 2016.

(51) Int. Cl.
*A61K 31/724* (2006.01)
*A61K 38/02* (2006.01)
*A61K 47/22* (2006.01)
*A61K 47/26* (2006.01)
*A61L 27/20* (2006.01)
*A61L 31/04* (2006.01)

(56) References Cited

OTHER PUBLICATIONS

International Search Report dated Apr. 26, 2017 for PCT International Application No. PCT/IB2017/050460, filed Jan. 27, 2017.
Written Opinion of the International Searching Authority dated Apr. 26, 2017for PCT International Applicaiton No. PCT/IB2017/050460, filed Jan. 27, 2017.
Guvendiren et al., Shear-Thinning Hydrogels for Biomedical Applications, Soft Matter, vol. 8, Oct. 17, 2011, p. 20.
Lu et al.:, Injectable Shear-Thinning Hydrogels engineered with a self-assembling Dock-and-Lock mechanism, Biomaterials, vol. 33, Dec. 16, 2011, pp. 2145-2153.
Charlot, Aurélia, and Rachel Auzély-Velty. "Synthesis of novel supramolecular assemblies based on hyaluronic acid derivatives bearing bivalent β-cyclodextrin and adamantane moieties." Macromolecules 40.4 (2007): 1147-1158.
Rodell, Christopher B., et al. "Shear-thinning supramolecular hydrogels with secondary autonomous covalent crosslinking to modulate viscoelastic properties in vivo." Advanced functional materials 25.4 (2015): 636-644.
Tan, Huaping, et al, "Controlled gelation and degradation rates of injectable hyaluronic acid-based hydrogels through a double crosslinking strategy." Journal of tissue engineering and regenerative medicine 5.10 (2011): 790-797.
WIPO/IB, International Preliminary Report on Patentability (Ch. 1), dated Jul. 31, 2018, re PCT International Patent Application No. PCT/IB2017/050460.
Lee Jeongwook, et al. "Phase Controllable Hyaluronic Acid Hydrogel with Iron (III) Ion-Catechol Induced Dual Cross-Linking by Utilizing the Gap of Gelation Kinetics." Macromolecules 4919 (2916): 7456-7459.

\* cited by examiner

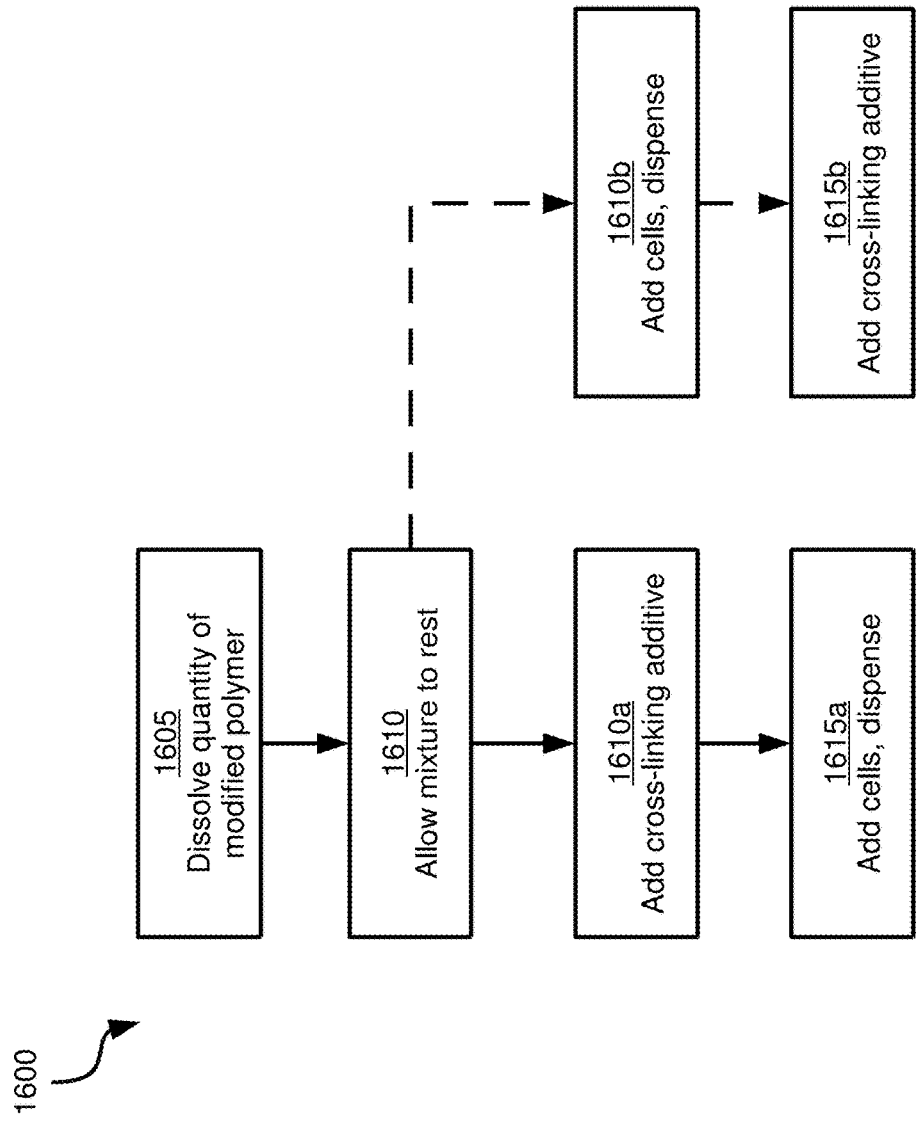

SHEAR-THINNING HYDROGEL, KIT AND METHOD OF PREPARATION

CROSS-REFERENCE TO RELATED APPLICATIONS

This application is a continuation of PCT application number PCT/IB2017/050460, filed Jan. 27, 2017, which claims priority to U.S. 62/288,778, filed Jan. 29, 2016, the entirety of which is incorporated herein by reference.

FIELD

The specification relates generally to hydrogels, and specifically to a shear-thinning hydrogel, as well as a kit and method for preparing the shear-thinning hydrogel.

BACKGROUND

Hydrogels have many applications in the fields of medicine and life sciences, particularly in tissue engineering and regenerative medicine (TERM). Tissue engineering involves the construction or reconstruction of animal (e.g. human) tissue using cells and other components found within tissue, such as extracellular matrix components. A goal of TERM is to develop transplantable tissue and organs to address issues associated with organ transplants, such as organ shortage and organ rejection. TERM can enable medical professionals to use a patient's own cells to create new tissue and organs for the patient.

Regenerative medicine is the clinical application of this TERM technology for the purpose of regenerating damaged organs or tissue and for conducting implants and transplants using engineered tissue or organs. A goal of regenerative medicine is to use a patient's own cells to create transplantable tissue and organs to address the issues of organ shortage and immune system rejection that occur when transplanting donated organs.

The field of tissue engineering also includes tumor engineering, the use of cancer cells to create tumors for testing and research purposes, as well as personalized medicine. These tumors are three-dimensional aggregates of cells which attempt to mimic the conditions that occur in cancer in humans and other animals. Such tumors can be used to test cancer drugs in vitro, and may allow for more accurate testing by better simulating the conditions under which tumours develop within animals (e.g. by simulating cell-cell and cell-matrix interactions and by providing an extracellular matrix).

Hydrogels are employed in tissue engineering and regenerative medicine, for example for the formation of three-dimensional biological scaffolds in vitro and in vivo, and in some cases ex vivo. Some applications require that the hydrogels be injectable, such as the use of 3D bioprinters and other injection devices to build the scaffolds, transplant organs, and the like. Further, such hydrogels typically are also expected to provide a certain degree of mechanical strength and stiffness to support cell growth.

The conflicting requirements of injectability (preferably without damaging cells or other materials suspended within the hydrogel) and mechanical strength can render the design of such hydrogels difficult. Physical cross-linking, for example, may be employed to provide some mechanical strength while still allowing the hydrogel to be injected. For example, PCT patent publication no. WO 2014028209 A1 describes a hydrogel with a guest-host cross-linking mechanism, which softens or liquefies under pressure (i.e. undergoes shear-thinning) to allow injection. PCT patent publication no. WO 2011084710 A1 discusses another type of cross-linking, based on metal-ligand complexes.

However, physical cross-linking may not have sufficient mechanical strength to provide a suitable extracellular matrix for the generation of simulated tumours and other structures.

SUMMARY

According to an aspect of the specification, a shear-thinning hydrogel composition is provided, comprising: a first polymer chain including: (i) a first plurality of units each having at least one of a monosaccharide and an amino acid; and (ii) a cross-linking group bound to the at least one of the monosaccharide and the amino acid of one of the first plurality of units via conversion of a carboxyl group of the unit to a peptide bond; a second polymer chain including a second plurality of the units; and a cross-linking additive connecting one of the second plurality of units to the first polymer chain via the cross-linking group.

According to another aspect of the specification, a kit is provided, comprising: a quantity of a powdered polymer including: (i) a plurality of units each having at least one of a monosaccharide and an amino acid; and (ii) a cross-linking group bound to the at least one of the monosaccharide and the amino acid of one of the first plurality of units via conversion of a carboxyl group of the unit to a peptide bond; and a quantity of a cross-linking additive for connecting first and second chains of the polymer via the cross-linking group.

According to a further aspect of the specification, a method of preparing a shear-thinning hydrogel composition is provided, comprising: preparing a solution of a first polymer chain including: (i) a first plurality of units each having at least one of a monosaccharide and an amino acid; and (ii) a cross-linking group bound to the at least one of the monosaccharide and the amino acid of one of the first plurality of units via conversion of a carboxyl group of the unit to a peptide bond; and mixing, into the aqueous solution, a cross-linking additive to cross-link first and second chains of the polymer.

BRIEF DESCRIPTIONS OF THE DRAWINGS

Embodiments are described with reference to the following figures, in which:

FIG. 16 depicts a method of preparing a shear-thinning hydrogel, according to a non-limiting embodiment.

DETAILED DESCRIPTION OF THE EMBODIMENTS

The present disclosure is directed to shear-thinning hydrogels. In general, the hydrogels described herein include a plurality of polymer chains, including hydrophilic polymer chains, including at least a first hydrophilic polymer chain and a second hydrophilic polymer chain. Each chain includes a plurality of repeating units; as will be discussed below, in some embodiments, each chain includes a plurality of units each containing at least one of a monosaccharide and an amino acid. One or more of the units of either or both of the first chain and the second chain includes a cross-linking group. In some embodiments, in which the units of the chain each include a monosaccharide, the cross-linking group can be bound to the monosaccharide or the amino acid via replacement of a carboxyl group by a peptide bond.

The hydrogel also includes a cross-linking additive, various examples of which will be discussed herein. The cross-linking additive connects a unit of the second chain mentioned above to a unit of the first chain. More specifically, the cross-linking additive interacts with a cross-linking group on each chain to establish a cross-link between the chains, thus imparting greater stiffness to the hydrogel than would exist in the absence of the cross-link. As will also be discussed below, the resulting hydrogel is also shear-thinning in at least certain stages of the preparation thereof.

Figure 1:
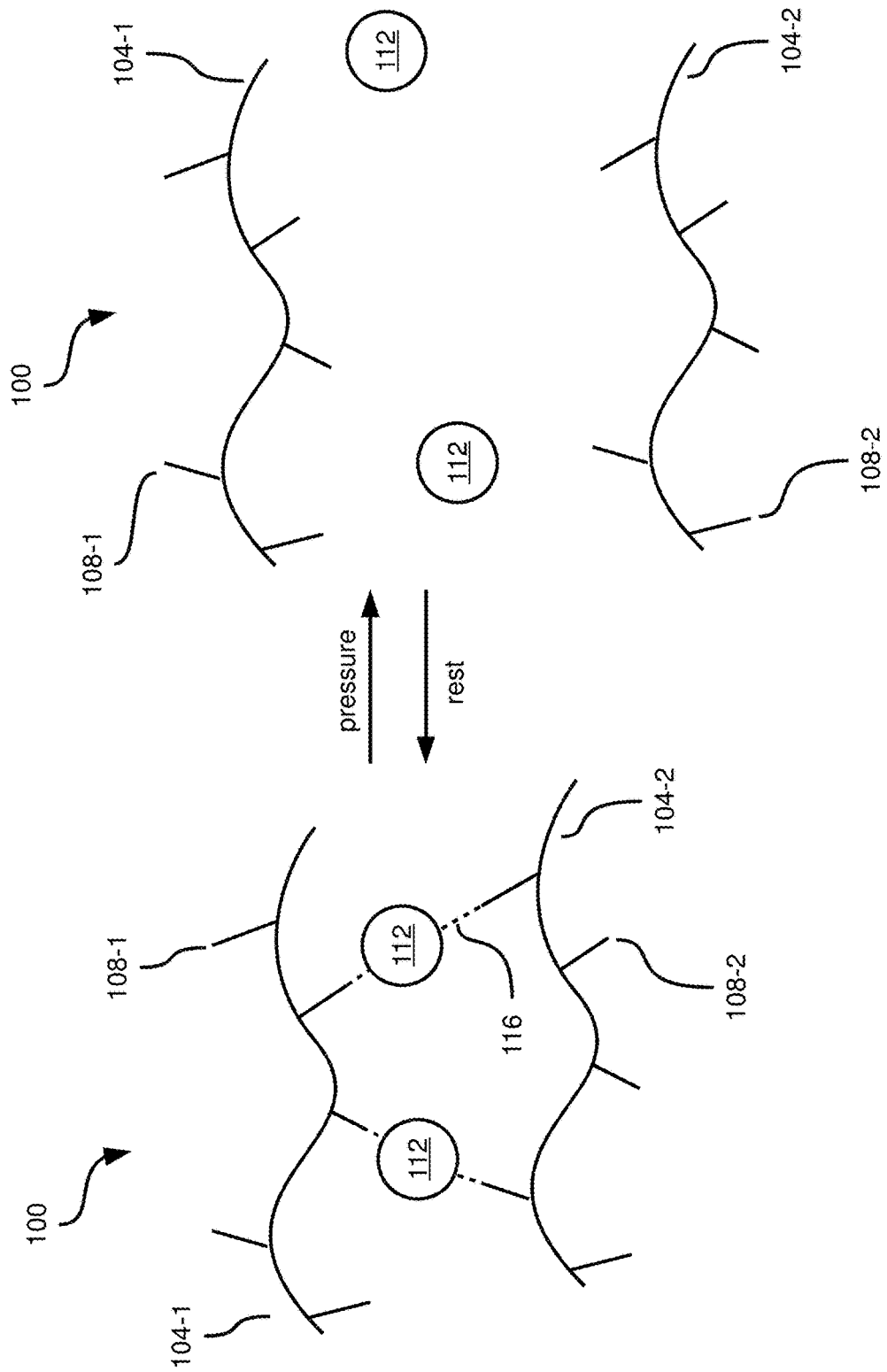
FIG. 1 depicts a shear-thinning hydrogel, according to a non-limiting embodiment.

Referring now to FIG. 1, a shear-thinning hydrogel 100 is depicted according to certain embodiments. The hydrogel 100 includes first and second hydrophilic polymer chains 104-1 and 104-2 (which may also be first and second segments of the same polymer chain), each including at least one cross-linking group 108-1, 108-2. The nature of the polymer chains 104 and the cross-linking groups 108 will be described below in greater detail. In addition, the hydrogel 100 includes a cross-linking additive 112 that establishes bonds 116 between respective pairs of cross-linking groups. As a result, each molecule of the cross-linking additive 112 establishes at least one cross-link between the first and second chains 104-1 and 104-2.

When sufficient pressure is applied to the hydrogel 100, as shown on the right side of FIG. 1, at least a subset of the bonds 116 are broken, and the hydrogel 100 transitions to an injectable state with a lower stiffness than the gel state shown on the left side of FIG. 1. Upon removal of the above-mentioned pressure (e.g. after injection is complete), the cross-linking additive molecules 112 are free to re-establish the bonds 116 with the cross-linking groups 108, and the hydrogel 100 returns to the stiffer (relative to the injectable state) gel state shown on the left side of FIG. 1. As will be discussed in greater detail herein, in other embodiments the bonds 116 established by the cross-linking additive 112 are unaffected by the application of pressure. Instead, in such embodiments, other cross-linking bonds (not shown in FIG. 1) are broken by the application of pressure.

Figure 2:
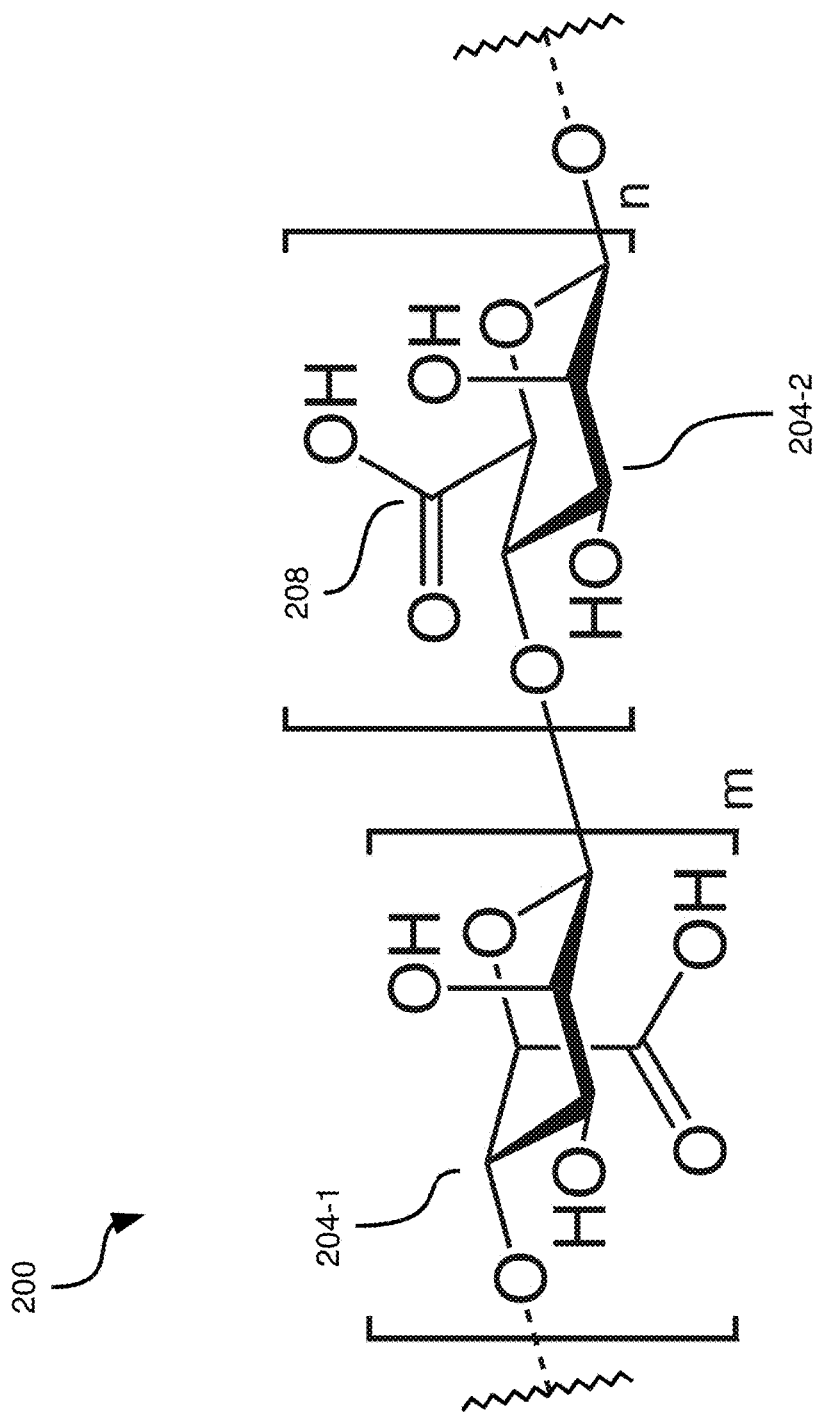
FIG. 2 depicts a unit of a polymer chain, according to a non-limiting embodiment.

As noted above, in some embodiments the hydrophilic polymer includes a plurality of repeating units each including a monosaccharide. Turning to FIG. 2, in an embodiment, the first and second polymer chains 104-1 and 104-2 include alginate (i.e. alginic acid) chains, and thus include a plurality of repeating units 200 each including a monosaccharide. In the embodiment shown in FIG. 2, each repeating unit 200 includes two saccharides, 204-1 and 204-2. Further, in the illustrated embodiment the monosaccharide (both 204-1 and 204-2 in this example) includes a carboxyl group 208.

Figure 3:
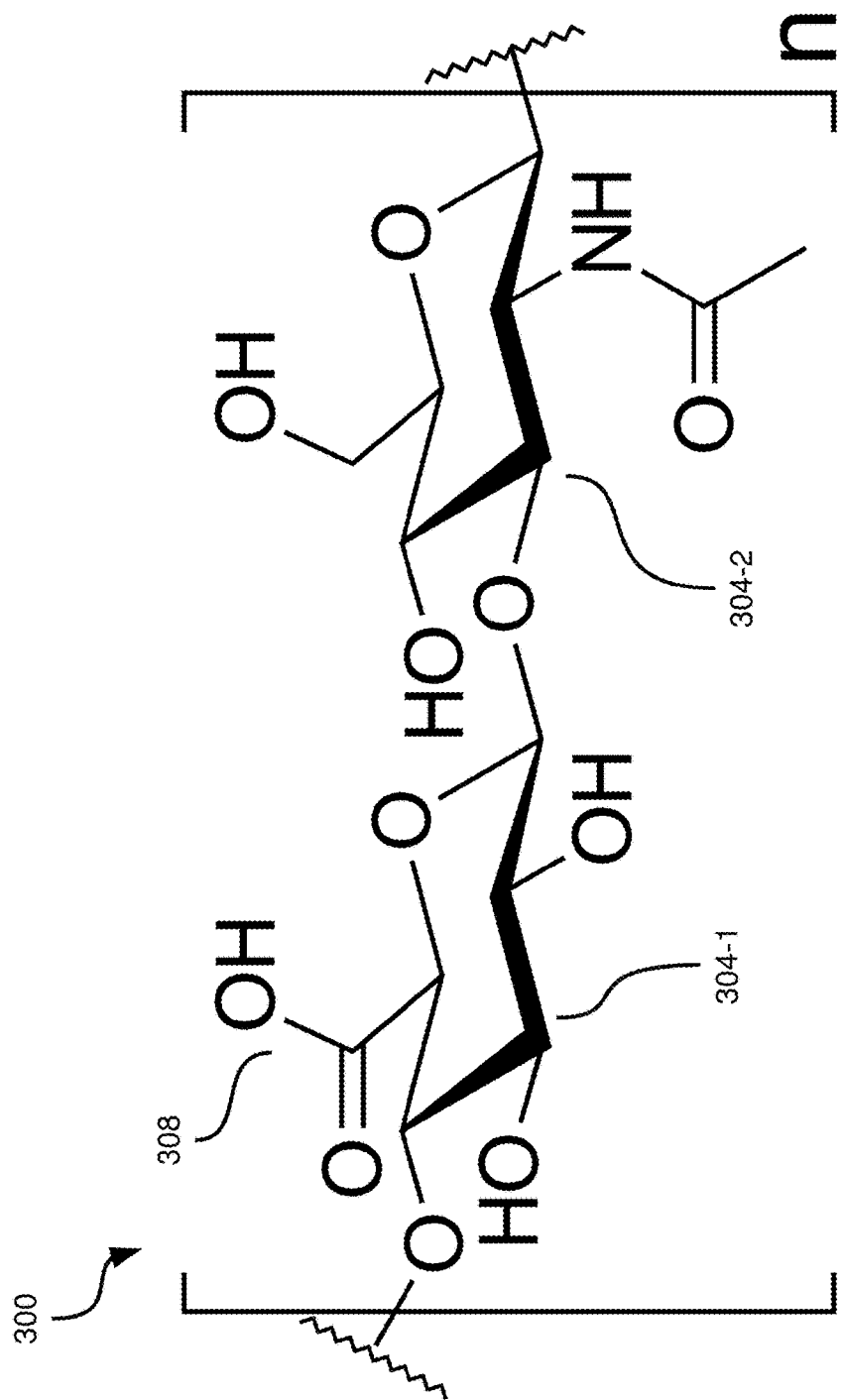
FIG. 3 depicts a unit of a polymer chain, according to another non-limiting embodiment.

Turning to FIG. 3, in other embodiments the first and second polymer chains 304-1 and 304-2 include hyaluronic acid. Thus each polymer chain 304 includes a plurality of repeating units 300. As with the embodiment of FIG. 2, each of the units 300 includes a monosaccharide; more specifically, the repeating unit 300 is a disaccharide (i.e. including two monosaccharides 304-1 and 304-2). Further, in the illustrated embodiment the monosaccharide (304-1 in this example) includes a carboxyl group 308.

In other embodiments (not shown), the polymer chains comprising the hydrogel 100 include a combination of hyaluronic acid and alginate. For example, in some embodiments the hydrogel 100 includes equal parts (by mass) hyaluronic acid and alginate. In other embodiments, the hydrogel 100 includes one part (by mass) of hyaluronic acid for two parts alginate. In further embodiments, the hydrogel can be composed entirely of hyaluronic acid, entirely of alginate, or of any intermediate mixture of the polymers. In embodiments in which alginate and hyaluronic acid are combined, either one of, or both of, the alginate and hyaluronic acid can include the cross-linking features discussed below.

In further embodiments, other polymers may be employed, including any one of, or any suitable combination of, agarose, alginate, RGD-modified alginate, chitosan, collagen, dextran, fibrin, gelatin, GelMA, glycogen, heparin, polyethylene glycol, poly(glycolic acid), poly(lactic acid), and poly(lactic acid-glycolic acid).

Figure 4:
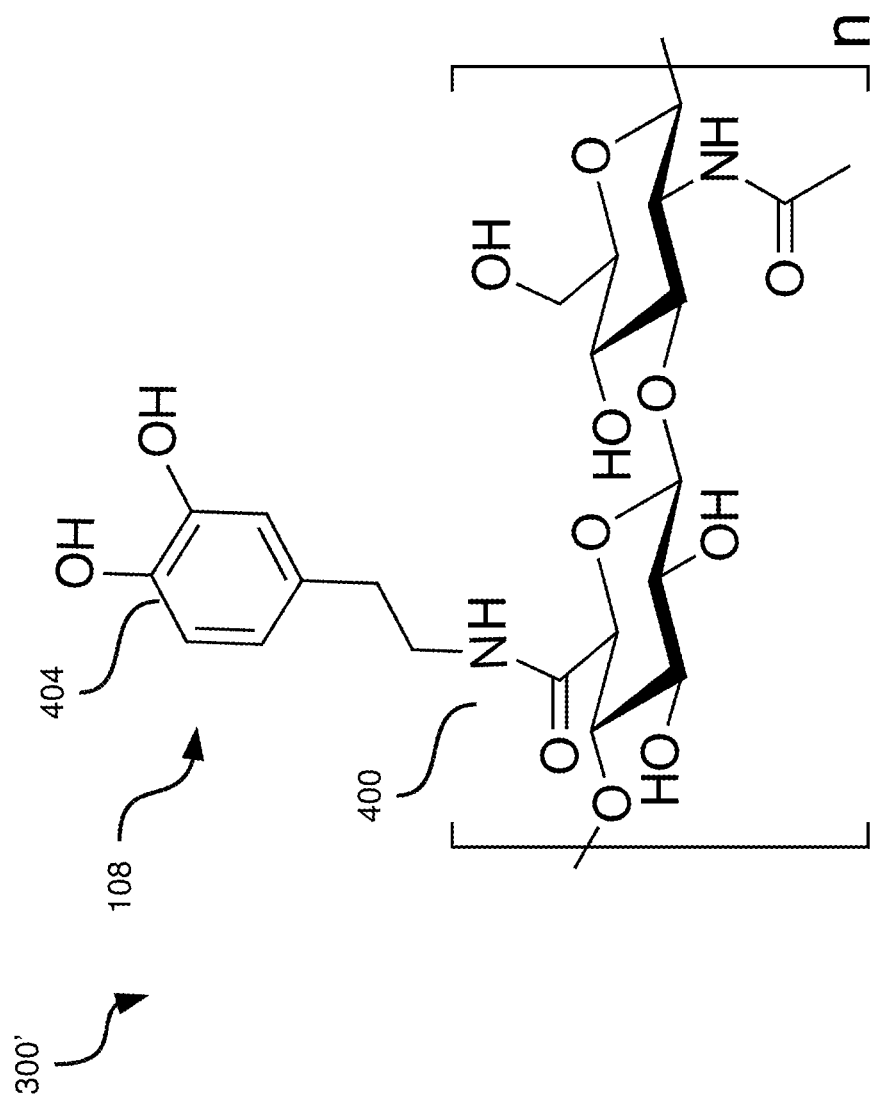
FIG. 4 depicts a cross-linking group bound to the unit of FIG. 3, according to a non-limiting embodiment.

As also noted earlier, one or more of the units 200, 300 of each of the polymer chains 104-1, 104-2 include a cross-linking group 108. Turning now to FIG. 4, in some embodiments in which hyaluronic acid is employed for at least a subset of the polymer chains in the hydrogel 100, the cross-linking groups 108 are each connected to units of the hyaluronic acid by replacement of the carboxyl group 308 (R—COOH) with a peptide bond (R—CONH). More specifically, as shown in FIG. 4, a modified version of the unit 300, labelled 300', is depicted with a cross-linking group connected by replacement of the carboxyl group with a peptide bond 400. In the example embodiment illustrated in FIG. 4, the cross-linking group 108 includes a ligand, such as a catechol group 404.

A variety of molecules can be employed to modify the unit 300 (or, indeed, the unit 200 or other suitable polymer units as will occur to those skilled in the art) to provide the catechol group 404. In the example of FIG. 4, the unit 300 has been modified with a molecule of dopamine to provide the catechol group 404. Other molecules can also be employed to provide the catechol group 404. For example, in some embodiments, the catechol group 404 is applied by bonding of a molecule of dopa to the unit 300. In still further embodiments, the catechol group 404 is applied by bonding of a molecule of epinephrine to the unit 300. Various other modifying molecules bearing catechol groups (e.g. norepinephrine) will also occur to those skilled in the art. In some embodiments, combinations of the above-mentioned molecules are employed to apply catechol groups to the polymer chains.

Further, various techniques will now be apparent to those skilled in the art for carrying out the modification of the base polymer with the catechol group 404, prior to preparation of the hydrogel 100.

In embodiments employing the catechol group 404 as the cross-linking group, the cross-linking additive 112 is a substance that binds to the hydroxyl groups of the catechol group 404. In the present embodiment, the cross-linking additive comprises a metal ion to be mixed with the modified base polymer (e.g. hyaluronic acid modified with dopamine, as set out above). Upon addition of the metal ion, typically in solution, to the polymer (which is typically dissolved in water, phosphate-buffered saline or the like), each metal ion establishes bonds with one or more cross-linking groups 108. Where two or more cross-linking groups are bonded to a given metal ion, cross-links are established between the corresponding polymer chains carrying the cross-linking groups.

Figure 5:
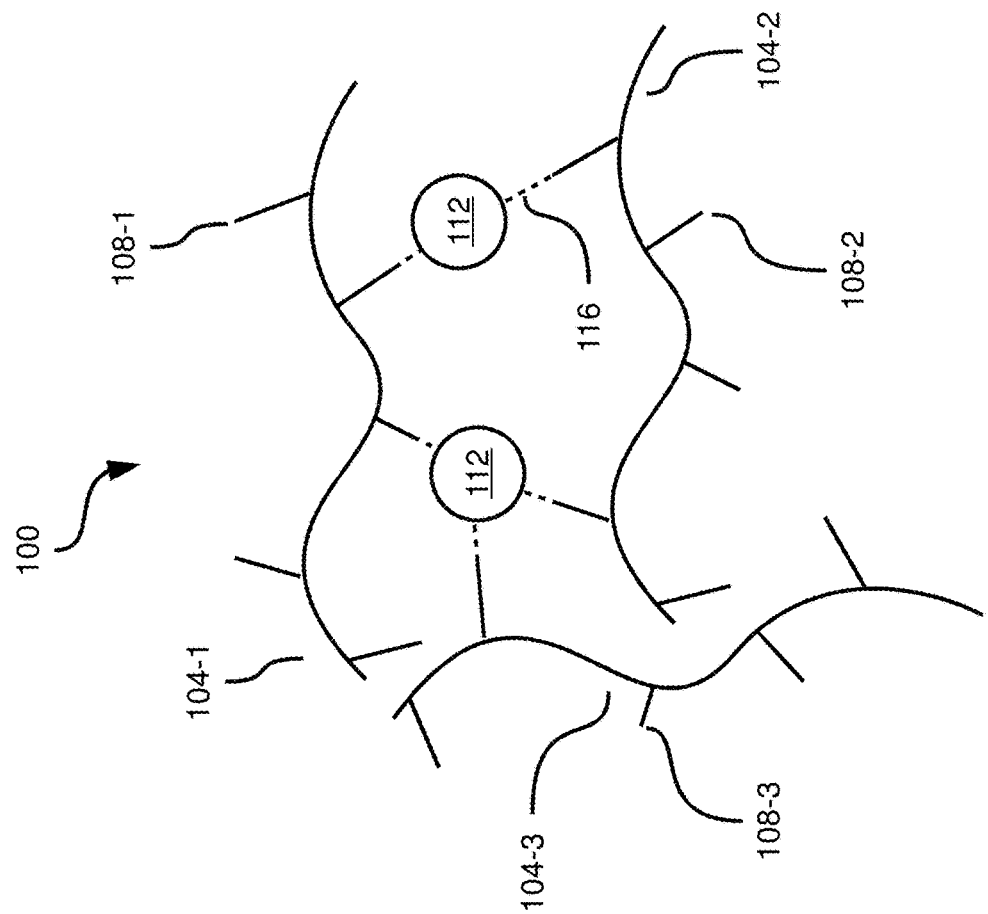
FIG. 5 depicts a shear-thinning hydrogel, according to another non-limiting embodiment.

Various metal ions are contemplated for use as the cross-linking additive 112. For example, the metal ion can be selected from iron, aluminum, chromium, copper and manganese. In some embodiments, a combination of metal ions can be employed as the cross-linking additive 112. In some embodiments, the oxidative state of the metal ion is 3+. In other embodiments, the oxidative state of the metal ion is 2+. In further embodiments, the oxidative state of the metal ion is 4+ (e.g. for manganese, titanium or the like). For metal ions with a 3+ state, each atom in the metal ion solution is able to form one, two or three links with respective catechol groups 404. Turning to FIG. 5, an example hydrogel 100 is shown in which a third polymer chain 104-3 (e.g. a hyaluronic acid chain having catechol groups bonded thereto as cross-linking groups 108) is cross-linked to both the chains 104-1 and 104-2 by a cross-linking additive particle (e.g. $Fe^{3+}$).

The number of cross-linking groups 108 to which each metal ion bonds is pH-dependent, due to the effect of the pH of the hydrogel 100 on the hydroxyl groups of the catechol group 404. More specifically, the Applicant has found that when the hydrogel 100 has a pH below approximately 5, each iron ion is most likely to bond with zero or one catechol groups (i.e. more likely than to bond with two or three catechol groups). When the hydrogel has a pH between approximately 5 and approximately 9, each iron ion is most likely to bond with two catechol groups, as shown in FIG. 1 and in one of the bonds of FIG. 5. Further, when the hydrogel has a pH above approximately 9, each iron ion is most likely to bond with three catechol groups, as shown in the left portion of FIG. 5.

Therefore, the pH of the hydrogel 100 is adjusted to obtain the desired level of metal-ligand cross-linking. In the present embodiment, the pH of the hydrogel 100 is adjusted (e.g. by addition of an acid such as hydrochloric acid, or a base such as sodium hydroxide) to a pH of between approximately 5 and approximately 9. For certain applications, a hydrogel with a greater stiffness may be desired, in which case the pH of the hydrogel 100 may be adjusted to above 9.

In further embodiments, other substances are contemplated for use as the cross-linking additive 112, and therefore cross-linking groups 108 other than the above-mentioned catechol groups 404 are employed. As noted earlier, in some embodiments the bonds 116 formed by the cross-linking additive 112 may not be those that break under pressure; instead, other types of cross-links may provide the shear-thinning property of the hydrogel.

Figure 6:
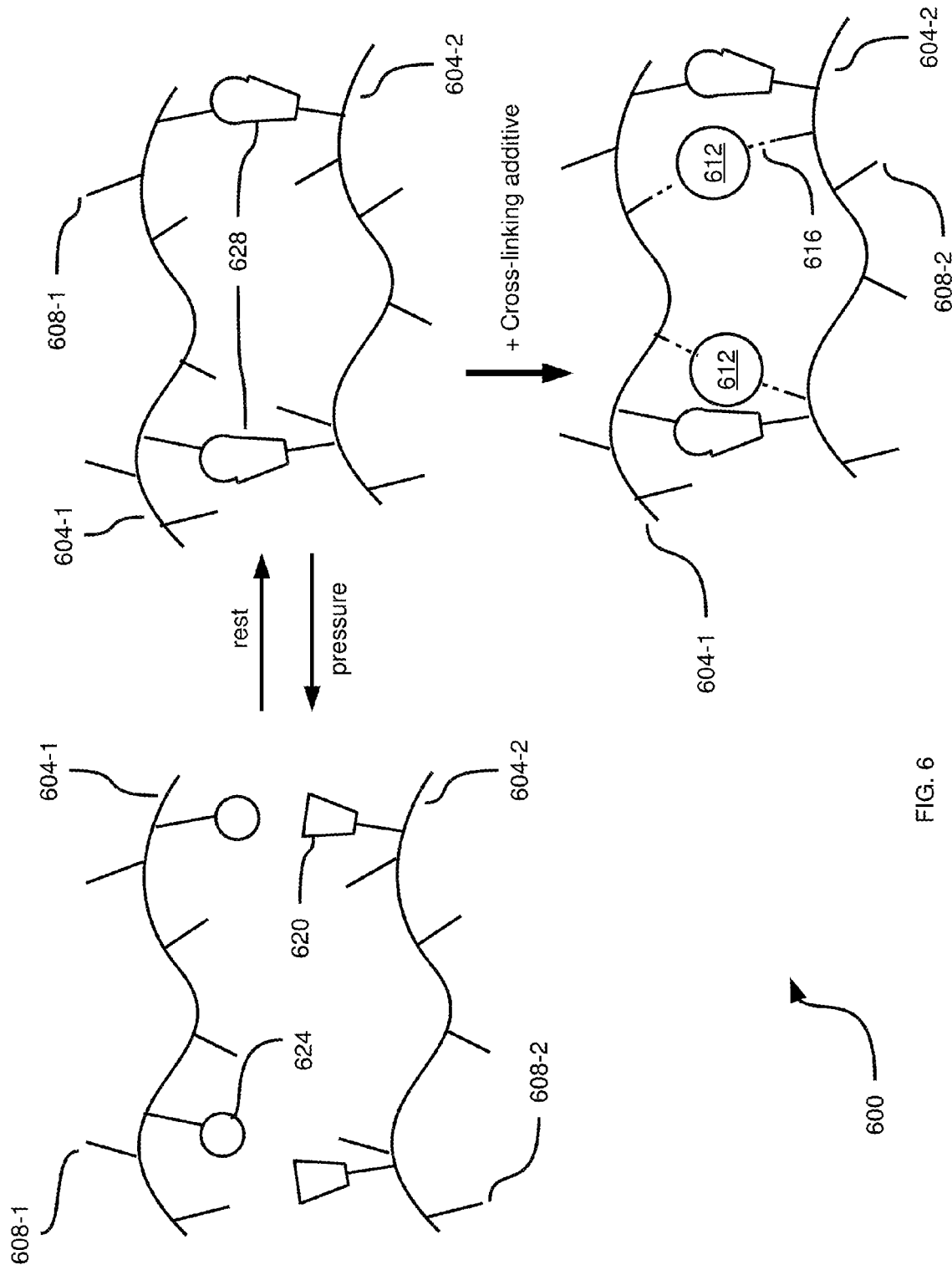
FIG. 6 depicts a shear-thinning hydrogel, according to a further non-limiting embodiment.

Accordingly, turning to FIG. 6, a shear-thinning hydrogel 600 is shown according to another embodiment. The hydrogel 600 includes a first hydrophilic polymer chain 604-1 and a second hydrophilic polymer chain 604-2, which are substantially as described above in connection with chains 104-1 and 104-2. In the present embodiment, it is contemplated that chains 604-1 and 604-2 are hyaluronic acid chains, with modifications as set out below. In other embodiments, various other polymers can be employed for chains 604-1 and 604-2, including alginate and mixtures of hyaluronic acid and alginate.

Figure 7:
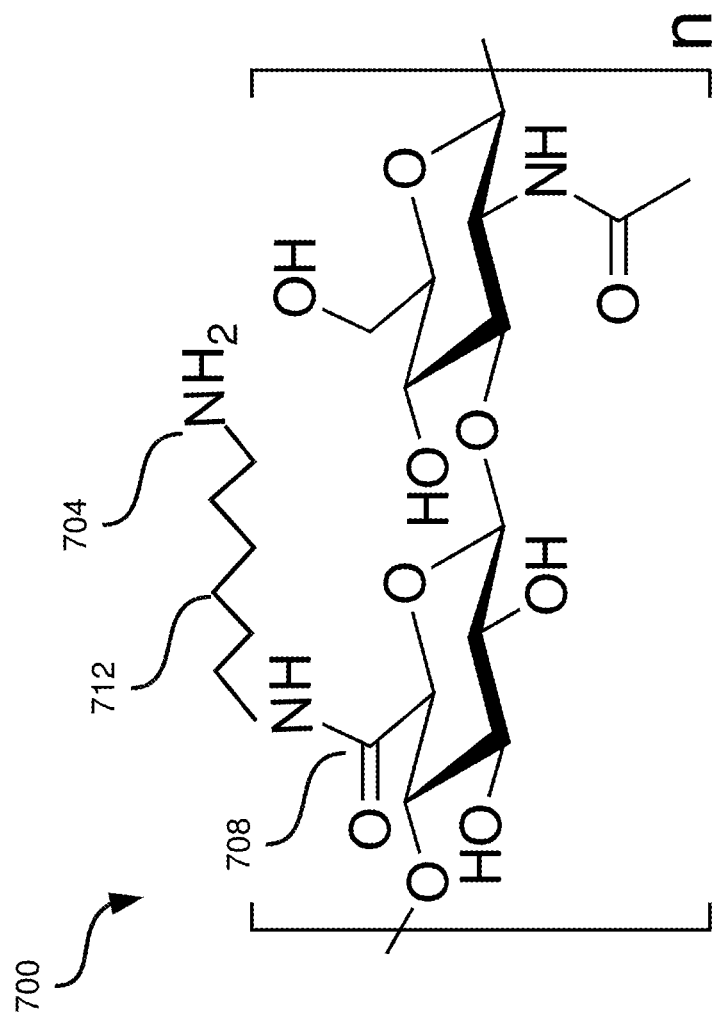
FIG. 7 depicts a cross-linking group bound to the unit of FIG. 3, according to another non-limiting embodiment.

The chains 604 include respective cross-linking groups 608-1 and 608-2, as well as a cross-linking additive 612 configured to cross-link the chains 604 via bonds 616 with the cross-linking groups 608. As set out earlier, the cross-linking groups 608 are connected to the polymer chains 604 via the replacement of a carboxyl group with a peptide bond. Referring to FIG. 7, a unit 700 of hyaluronic acid is depicted with an amine cross-linking group 704 connected thereto by a peptide bond 708 and a carbon chain 712. The length of the chain 712 need not be exactly as shown.

Figure 8:
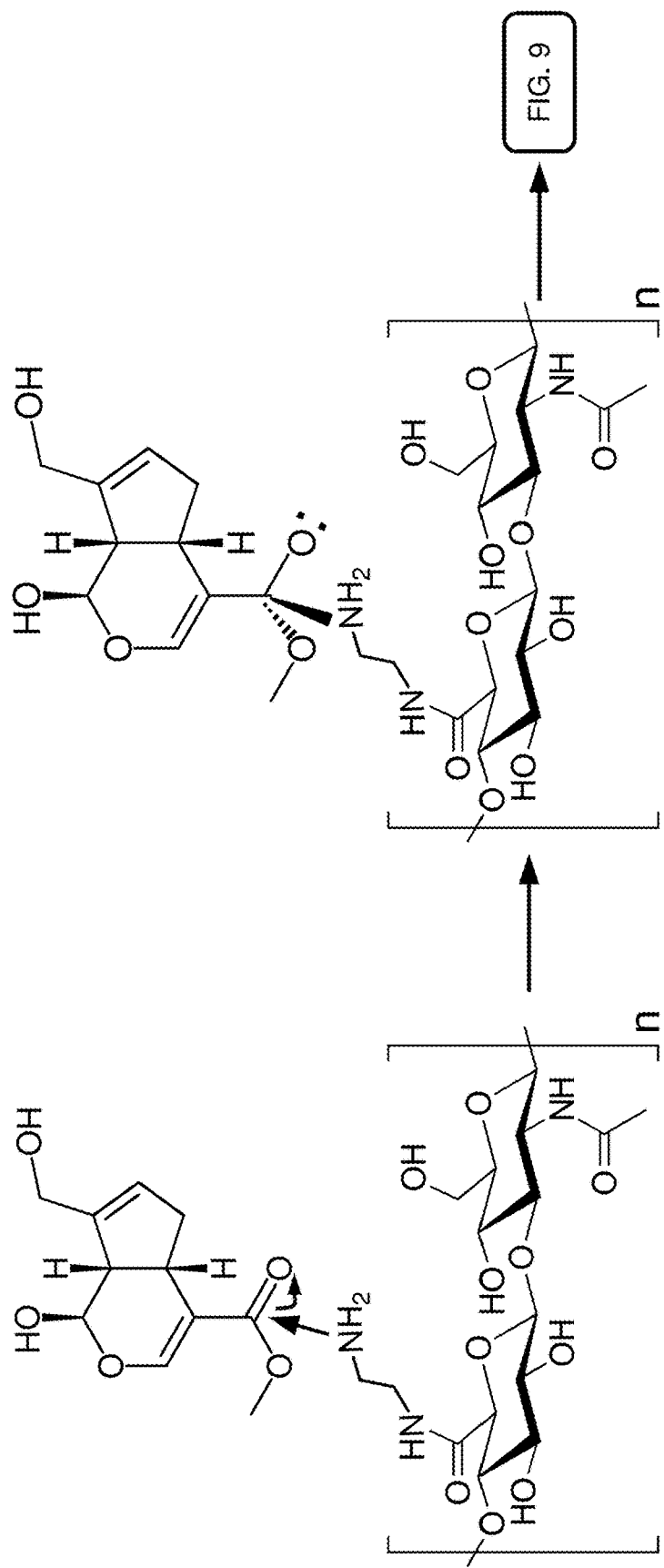
FIGS. 8-11 depict the formation of a cross-link with the hydrogel unit of FIG. 7, according to a non-limiting embodiment.
Figure 9:
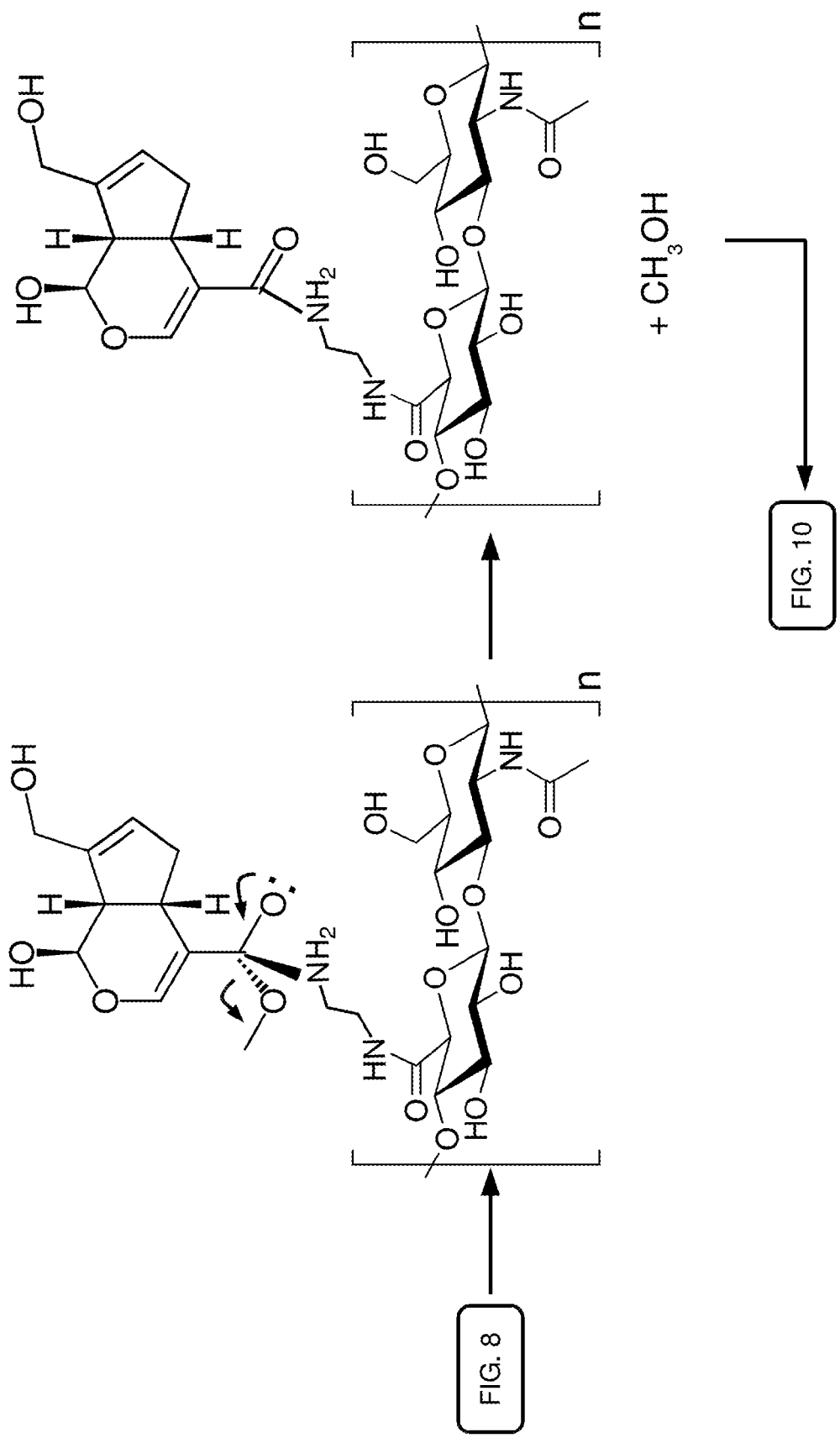
Figure 10:
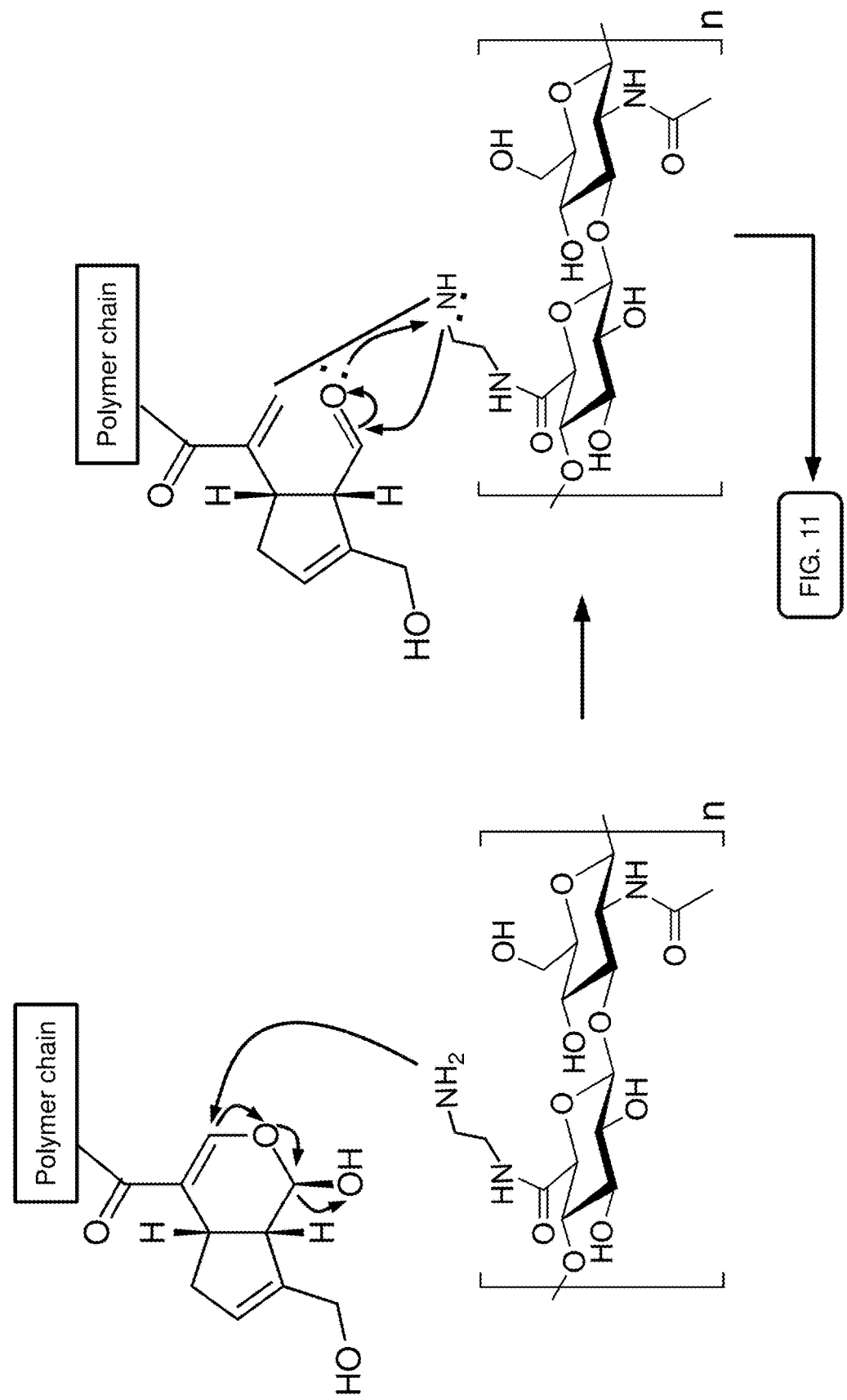
Figures 10, 11:
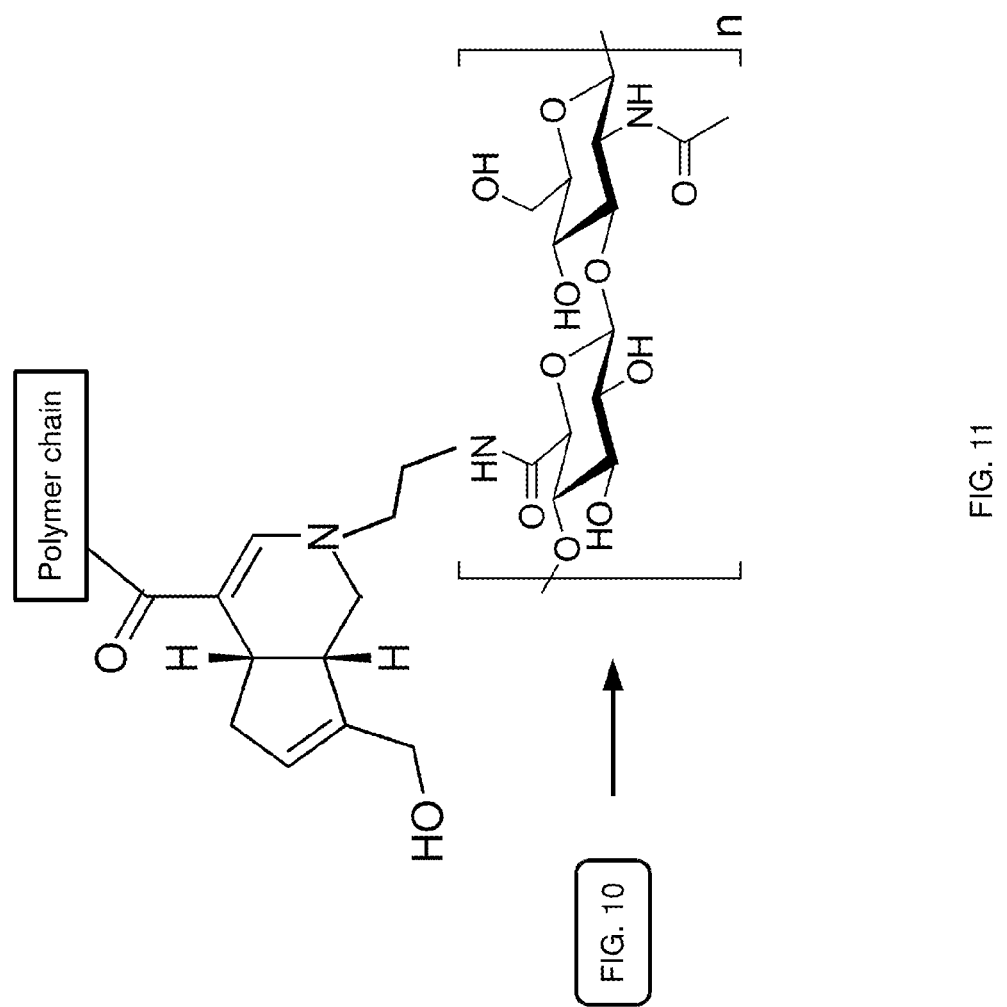
Figure 12:
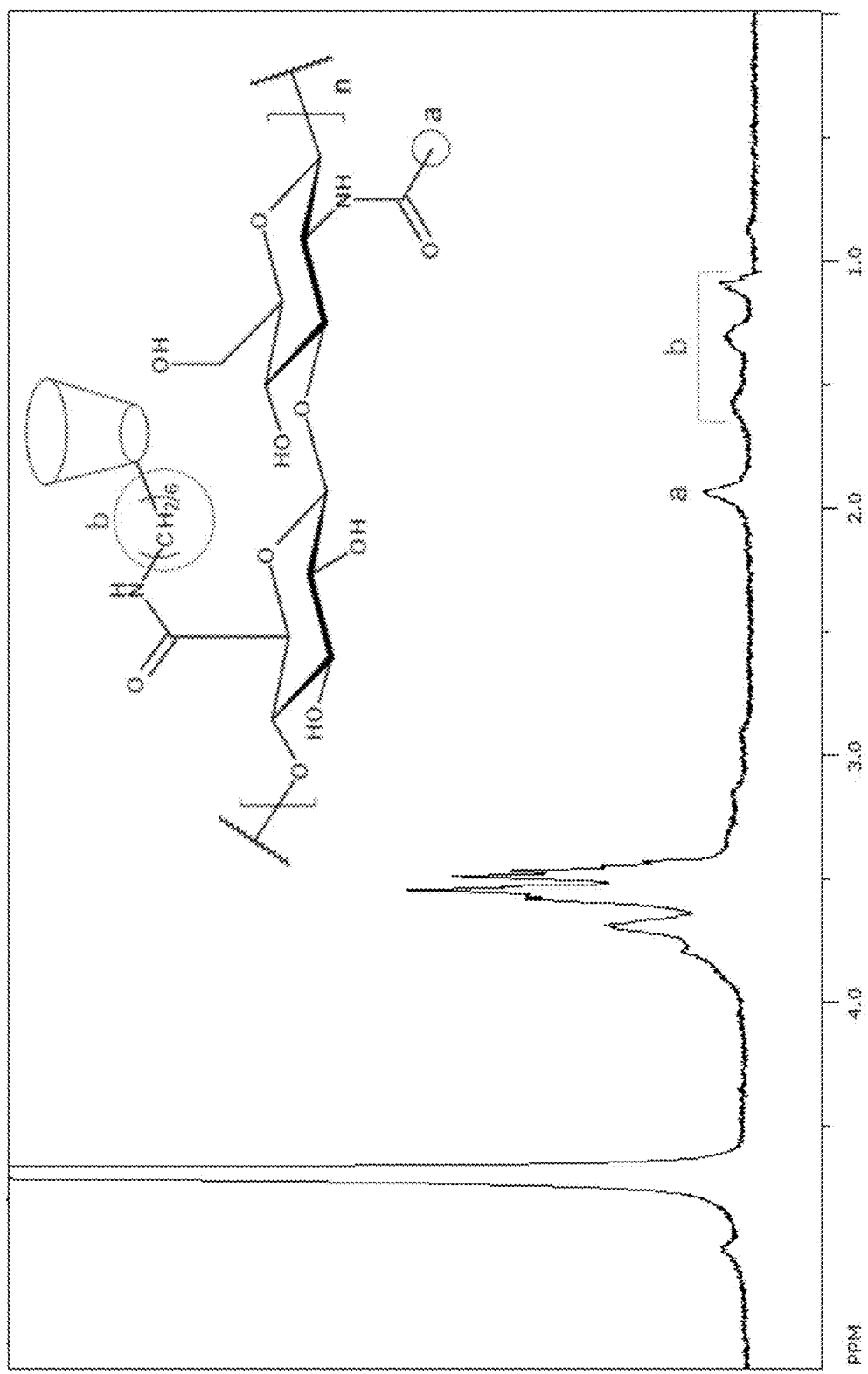
FIGS. 12-15 depict NMR plots for various components of a shear-thinning hydrogel, according to a non-limiting embodiment.
Figure 13:
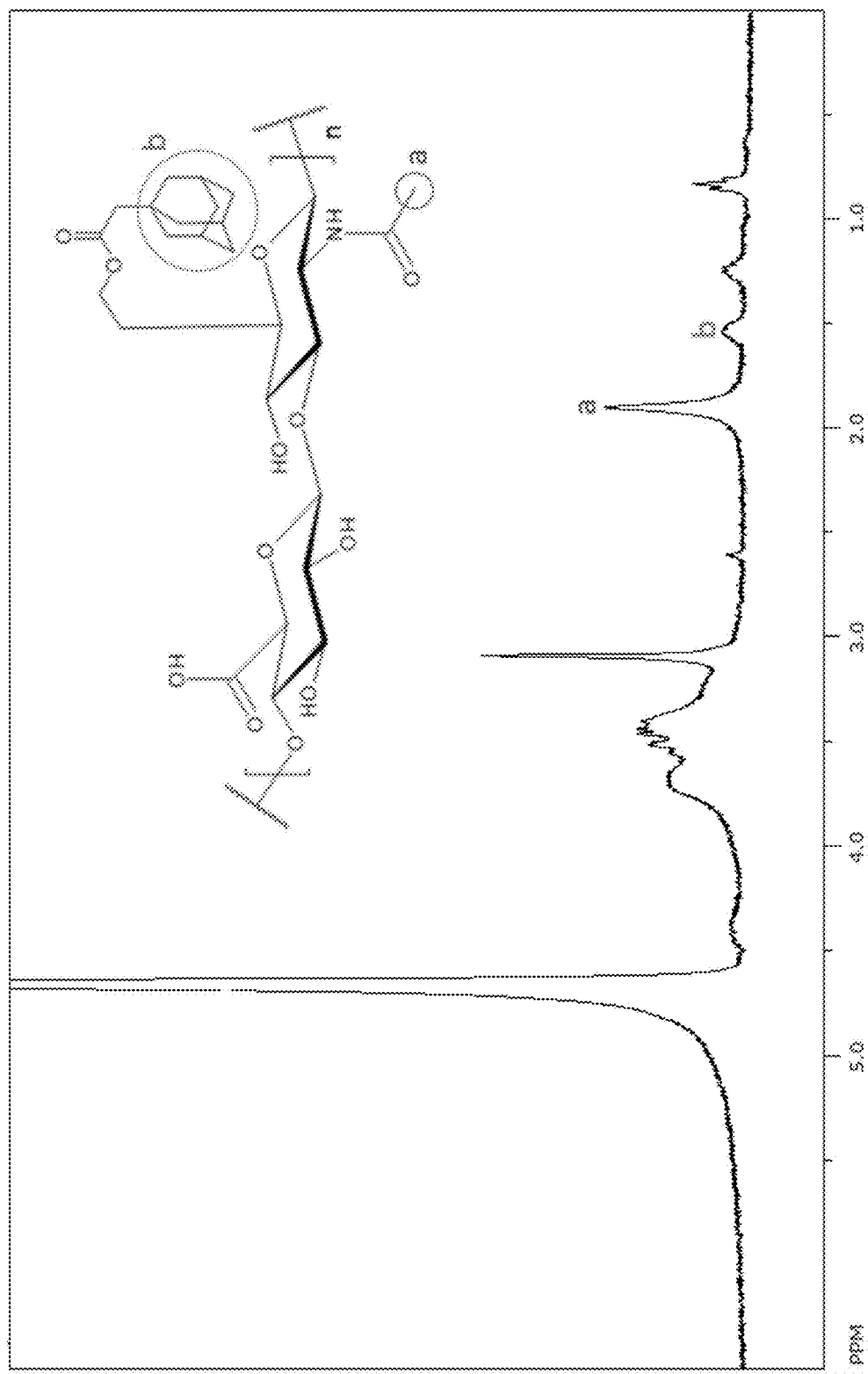
Figure 14:
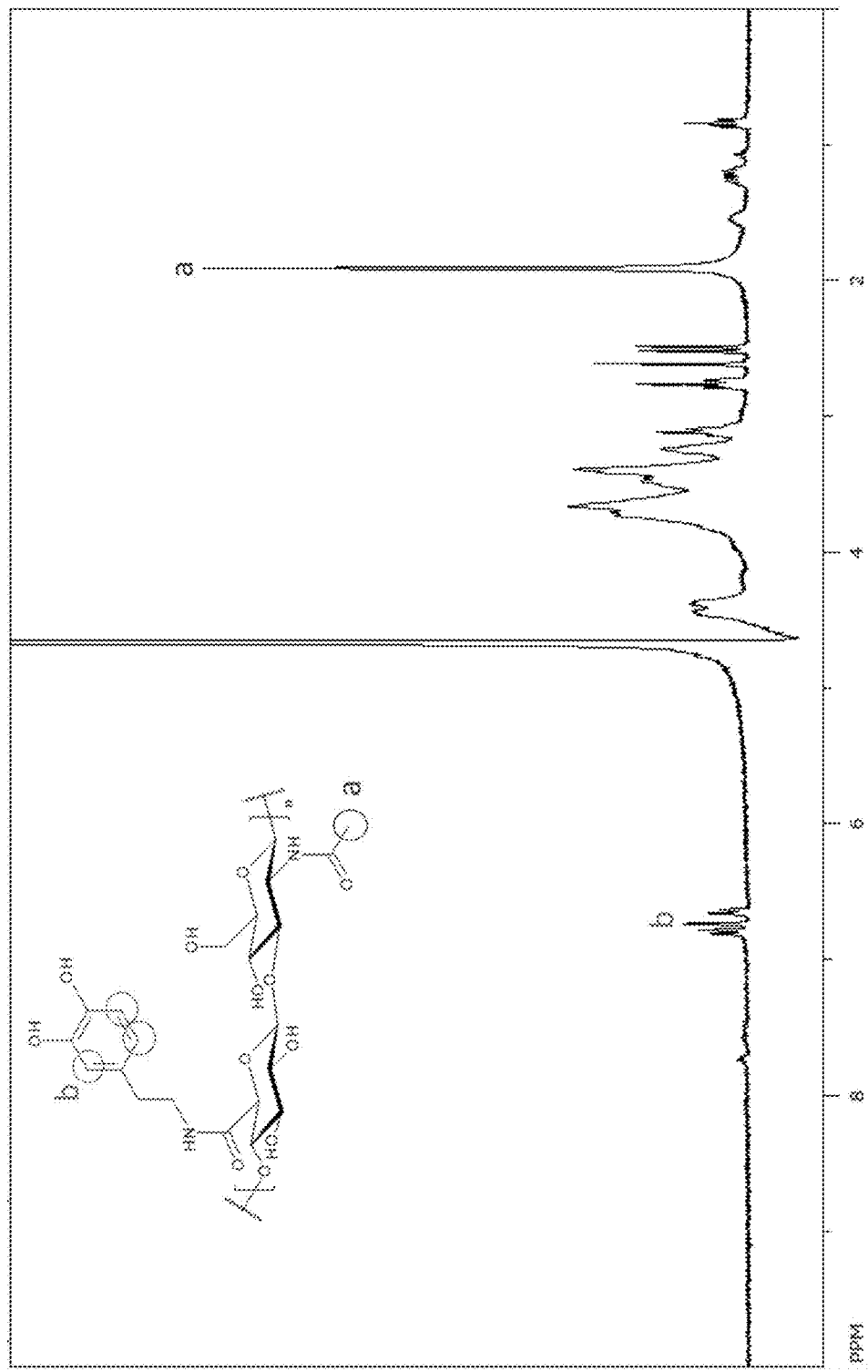
Figure 15:
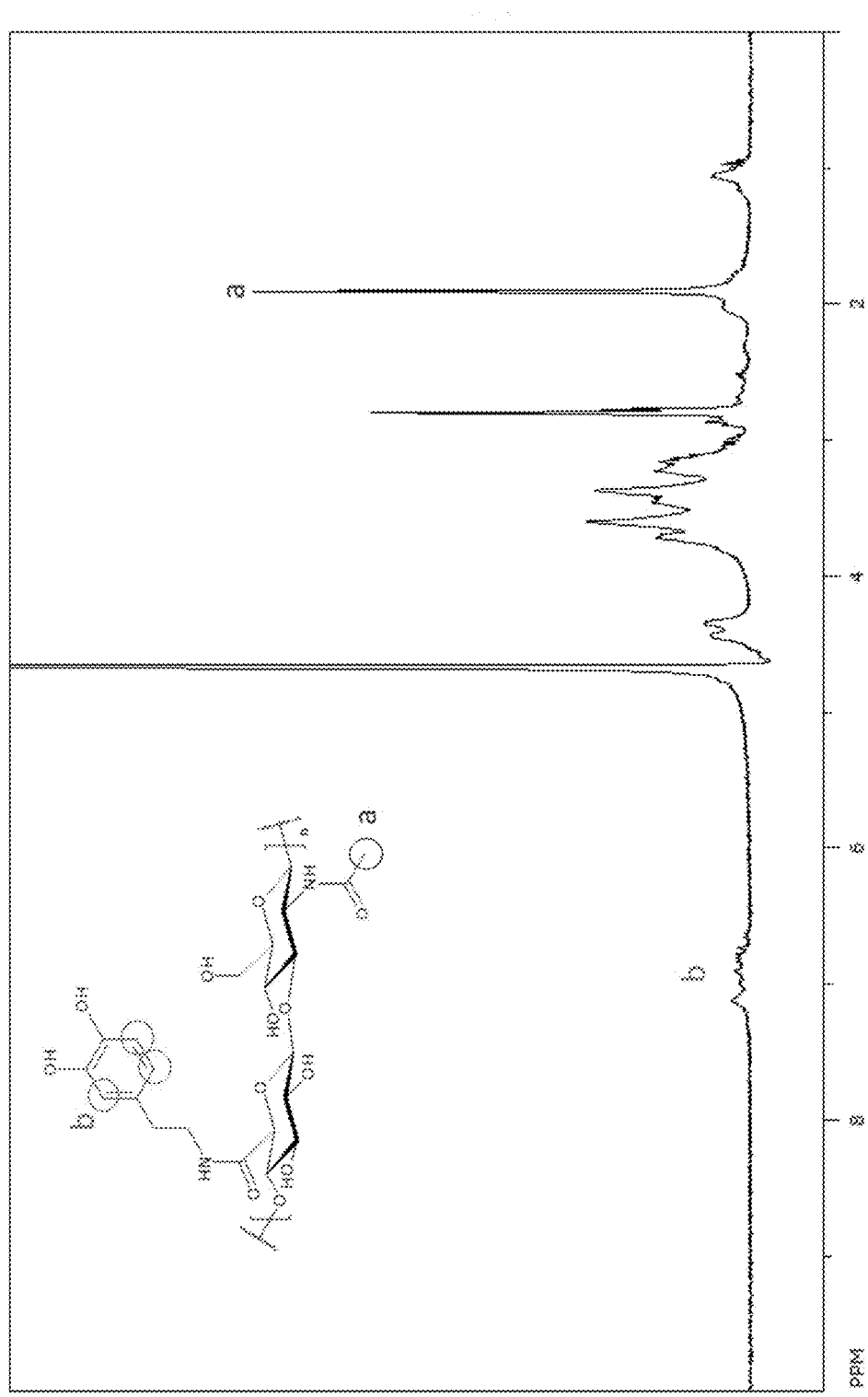

Returning to FIG. 6, as illustrated in the lower-right portion of the drawing, the cross-linking additive 612 establishes bonds 616 with cross-linking groups 608 on each of the first and second chains 604 to cross-link the chains 604. In the present embodiment, in which the cross-linking groups 608 are amine groups as illustrated in FIG. 7, the cross-linking additive 612 is a bridging molecule such as genipin, each molecule of which can interact with two amine groups to form a cross-link between the chains 604. FIGS. 8-9 depict the bonding of a molecule of genipin to a first amine group (e.g. on the chain 604-1), and FIGS. 10-11 depict the bonding of that molecule of genipin to a second amine group (e.g. on the chain 604-2). As will be apparent to those skilled in the art, the illustrated units of the first and second polymer chains conduct nucleophilic attacks on the molecule of genipin, resulting in a crosslink between the polymer chain units.

In other embodiments, the cross-linking additive includes other molecules; for example rose bengal is employed as a cross-linking additive in certain embodiments. In those embodiments, the cross-linking groups include furan groups, connected to the polymer chain via a peptide bond, rather than the amine groups discussed above. Further, in such embodiments rose bengal acts as a photo-initiator, bonding polymer chains via the above-mentioned furan groups in the presence of visible light, without becoming part of the bonds itself.

Referring again to FIG. 6, in the embodiment discussed above, in which the cross-linking additive 612 is genipin, the bonds 616 typically do not break under the application of pressure (e.g. during injection of the hydrogel 600). In this embodiment, the shear-thinning property is instead provided at an earlier stage of the preparation of the hydrogel 600. More specifically, the first chain 604-1 includes at least one guest cross-linking group 624. In the present example, the guest cross-linking group 624 is connected to a unit of the second chain via esterification. Further, the second polymer chain 604-2 includes at least one host cross-linking group 620 connected to the chain 604-2, for example, by the replacement of a carboxyl group with a peptide bond. Thus, some units of the chain 604-2 include a host cross-linking group, while other units include an amine group as discussed above.

More specifically, in some embodiments the host cross-linking group 620 is cyclodextrin, and the guest cross-linking group 624 is adamantane. Other suitable host and guest groups will also occur to those skilled in the art. As seen in FIG. 6, cyclodextrin and adamantane bond to each other to form a guest-host complex 628, which may be broken under pressure, thus providing a shear-thinning property to the hydrogel 600. When genipin is employed as the cross-linking additive, the addition of genipin begins a substantially irreversible stiffening process in the hydrogel 600, with the secondary cross-linking bonds 616 providing additional mechanical strength to the hydrogel 600.

Various other embodiments of the hydrogels discussed above are also contemplated. For example, in other embodiments, the amine-genipin cross-links of the hydrogel 600 can be replaced by another cross-linking mechanism, such as the metal-ligand mechanism discussed earlier herein. Further, in some embodiments both of the types of cross-linking additive discussed above can be employed, with or without the use of a guest-host mechanism. In other words, in addition to (optionally) the guest and host complexes, each polymer chain can include respective subsets of units carrying amine groups and catechol groups.

The hydrogels 100 and 600 are prepared, in certain embodiments, from a kit of materials. The kit includes a quantity of a powdered hydrophilic polymer including a plurality of units each having a monosaccharide, and a cross-linking group bound to the monosaccharide of one of the first plurality of units via conversion of a carboxyl group of the unit to a peptide bond. That is, the kit includes at least an amount of powdered polymer such as alginate or hyaluronic acid (or a combination of the two polymers), modified with a cross-linking group. In embodiments employing a guest-host mechanism as shown in FIG. 6, the kit includes two separately-stored quantities of powdered modified hydrophilic polymer.

The first quantity includes the polymer (modified with the cross-linking group as mentioned above) further modified with a host cross-linking group such as cyclodextrin. The second quantity includes the polymer (modified with the cross-linking group as mentioned above) further modified with a guest cross-linking group compatible with the host group, such as adamantane.

As noted earlier, techniques for the preparation of the various modifications to base polymer chains are familiar to those skilled in the art. The modifications may be verified, for example by way of nuclear magnetic resonance (NMR) studies. FIGS. 12, 13, 14 and 15 depict NMR results for chains of hyaluronic acid modified with, respectively, cyclodextrin, adamantane, dopamine (employing dimethyl sulfoxide, DMSO, for synthesis of the modified polymer), and dopamine (employing aqueous synthesis of the modified polymer).

The kit further includes a quantity of the cross-linking additive (e.g. a metal ion in solution, genipin or other suitable additive). When multiple additives are to be employed, the kit may include separately-stored quantities of each cross-linking additive.

In some embodiments, the kit also includes an amount of a filler polymer, which is not modified as discussed above. For example, the kit can include a quantity of powdered modified hyaluronic acid, and a further quantity of unmodified powdered alginate.

Turning to FIG. 16, a method 1600 of preparing the hydrogel 100, 600 is depicted according to certain embodiments. At block 1605, a quantity of polymer modified with a cross-linking group is dissolved in water, tris-buffered saline (TBS), phosphate-buffered saline (PBS), or any other suitable solvent. When a guest-host mechanism is employed, at block 1605 the two quantities may be dissolved together or separately and then mixed together. In embodiments in which a filler polymer is employed, the filler polymer is also dissolved at block 1605, either separately from the modified polymer for subsequent mixing, or together with the modified polymer.

In some embodiments, the amount of polymer is less than about 15 percent by mass of the hydrogel. In other embodiments, the amount of polymer is less than about 10 percent by mass of the hydrogel. In further embodiments, the amount of polymer is less than about 5 percent by mass of the hydrogel. Further, in embodiments in which a guest-host mechanism is employed, the guest and host-modified polymers are typically employed in equal proportions. In other embodiments, the guest and host-modified polymers are employed in different proportions. Where a filler (i.e. unmodified) polymer is employed, the filler polymer can represent up to twice the total amount of polymer in the hydrogel than the modified polymer. Thus, an example hydrogel prepared according to the method 1600 may include 5% by mass modified hyaluronic acid, and 10% by mass unmodified alginate. Further, the cross-linking additive is typically less than 10% by mass of the hydrogel.

The preparation of the dissolved polymer at block 1605 includes heating the solution during preparation to accelerate dissolution of the polymer powder(s), in some embodiments. For example, the solution may be heated to about 30° C. in some embodiments. In other embodiments, the solution may be heated up to, but not beyond, the degradation temperature of the polymer (e.g. about 60° C. for hyaluronic acid).

Following the performance of block 1605, the mixture is allowed to rest for a period of time. For example, the mixture may be left for 24 hours, although greater or smaller time periods may also be employed. Block 1610 can also be omitted in some embodiments, particularly those not employing a guest-host mechanism.

After the performance of block 1610 (or block 1605, if block 1610 is omitted), the method 1600 proceeds to either of block 1610a or 1610b. At block 1610a, the cross-linking additive is added to the solution, and then at block 1615a the resulting hydrogel is dispensed via any suitable mechanism. For example, syringes, pipettes, 3D printers, syringe pumps, dispensing machines, high-throughput screening systems, and automated or manual injection and extrusion systems may be employed at block 1615a.

As will now be apparent, the addition of cross-linking additive at block 1610a begins the mechanical strengthening of the hydrogel via the formation of cross-linking bonds (in addition to those formed by guest-host complexes at block 1610, if such complexes are employed). As noted earlier, when the cross-linking additive is genipin, the resulting cross-links are typically not breakable under pressure, and therefore the performance of block 1615a typically follows the performance of block 1610a closely in time (e.g. within about thirty minutes) for such materials.

Further, when the cross-linking additive is a metal ion, the resulting cross-links typically form more quickly than those formed by genipin. Further, the resulting metal-ligand bonds may be more resistant to breaking under pressure than the guest-host bonds. Therefore, when a metal-ligand mechanism is employed, the performance of block 1615a typically follows the performance of block 1610a closely in time (e.g. within about five minutes).

Alternatively to the performance of blocks 1610a and 1615a, the performance of method 1600 can instead proceed from block 1610 (or 1605, when block 1610 is omitted) to block 1610b. At block 1610b, cells (e.g. tumour cells) are added to the hydrogel as needed, and the hydrogel is dispensed as described above. The cross-linking additive is then added to the hydrogel after dispensing. For example, a metal ion in solution may be added to each well in a 96-well plate after the wells have been filled with hydrogel suspending tumour cells. The performance of blocks 1610b and 1615b may be desirable for fast-acting formulations, such as those employing the metal-ligand mechanism. In further embodiments, the performance of method 1600 can include the addition of both cells and cross-linking additive(s), followed by dispensing the hydrogel.

Various applications may make use of hydrogels as described herein. For example, the hydrogels described above may be employed in personalized drug testing, such that a plurality of simulated tumours (e.g. in a 96-well plate) may be seeded with patient cells supported within a hydrogel matrix. Various different prospective drugs may then be applied to the wells, and their effects on cell viability monitored (e.g. via ATP assays).

Certain advantages to the hydrogels described herein will be apparent to those skilled in the art. For example, the use of hyaluronic acid in certain embodiments may better simulate the biological environment of cells (as hyaluronic acid also appears in the extracellular environment in vivo).

The scope of the claims should not be limited by the embodiments set forth in the above examples, but should be given the broadest interpretation consistent with the description as a whole.

The invention claimed is:

1. A shear-thinning hydrogel composition, comprising:
   a first polymer chain including:
   (i) a first plurality of units of hyaluronic acid, each unit having at least one monosaccharide;
   (ii) a further plurality of units of alginate bound to the first plurality of units; and
   (iii) a cross-linking group comprising dopamine bound to the at least one monosaccharide of one of the first plurality of units via conversion of a carboxyl group of the unit to a peptide bond;
   a second polymer chain including a second plurality of the units;
   a cross-linking additive comprising $Fe^{2+}$ connecting one of the second plurality of units to the first polymer chain via the cross-linking group; and
   collagen.

2. The shear-thinning hydrogel composition of claim 1, wherein the cross-linking group comprises a first ligand group; and
   wherein the one of the second plurality of units comprises a second ligand group, the cross-linking additive connecting to each of the first ligand group and the second ligand group.

3. The shear-thinning hydrogel composition of claim 2, wherein the ligand group and the second ligand group each comprise a catechol group.

4. The shear-thinning hydrogel composition of claim 1, wherein the first and second polymer chains represent less than 15% by mass of the composition.

5. The shear-thinning hydrogel composition of claim 1, wherein the first and second polymer chains represent less than 10% by mass of the composition.

6. The shear-thinning hydrogel composition of claim 1, wherein the first and second polymer chains represent less than 5% by mass of the composition.

7. The shear-thinning hydrogel composition of claim 4, the remainder of composition comprising at least one of: water, tris-buffered saline, and phosphate-buffered saline.

8. The shear-thinning hydrogel composition of claim 5, the remainder of the composition comprising at least one of: water, tris-buffered saline, and phosphate-buffered saline.

9. The shear-thinning hydrogel composition of claim 6, the remainder of the composition comprising at least one of: water, tris-buffered saline, and phosphate-buffered saline.

* * * * *